(12) United States Patent
Themelis

(10) Patent No.: US 11,071,474 B2
(45) Date of Patent: Jul. 27, 2021

(54) APPARATUS AND METHOD FOR TRACKING A MOVABLE TARGET

(71) Applicant: Leica Instruments (Singapore) Pte. Ltd., Singapore (SG)

(72) Inventor: George Themelis, Lindau (DE)

(73) Assignee: Leica Instruments (Singapore) Pte. Ltd., Singapore (SG)

(*) Notice: Subject to any disclaimer, the term of this patent is extended or adjusted under 35 U.S.C. 154(b) by 313 days.

(21) Appl. No.: 16/015,961

(22) Filed: Jun. 22, 2018

(65) Prior Publication Data
US 2019/0008420 A1 Jan. 10, 2019

(30) Foreign Application Priority Data

Jul. 7, 2017 (EP) .................................... 17180286

(51) Int. Cl.
*A61B 5/05* (2021.01)
*A61B 5/11* (2006.01)
*A61B 90/00* (2016.01)
*A61B 34/20* (2016.01)
*A61B 5/00* (2006.01)
*A61B 5/055* (2006.01)
(Continued)

(52) U.S. Cl.
CPC .......... *A61B 5/1127* (2013.01); *A61B 5/0071* (2013.01); *A61B 5/055* (2013.01); *A61B 6/485* (2013.01); *A61B 8/481* (2013.01); *A61B 34/20* (2016.02); *A61B 90/39* (2016.02); *A61B 2034/2065* (2016.02); *A61B 2090/395* (2016.02); *A61B 2090/3908* (2016.02); *A61B 2090/3925* (2016.02); *A61B 2090/3933* (2016.02); *A61B 2090/3941* (2016.02); *A61B 2090/3954* (2016.02); *A61B 2090/3966* (2016.02); *A61B 2090/3987* (2016.02)

(58) Field of Classification Search
None
See application file for complete search history.

(56) References Cited

U.S. PATENT DOCUMENTS

| 5,772,593 A | 6/1998 | Hakamata | |
|---|---|---|---|
| 2004/0010192 A1* | 1/2004 | Benaron | B82Y 10/00 600/431 |

(Continued)

FOREIGN PATENT DOCUMENTS

| WO | 99/27839 A2 | 6/1999 |
|---|---|---|
| WO | 2008/128051 A2 | 10/2008 |
| WO | 2014175853 A1 | 10/2014 |

*Primary Examiner* — Joel F Brutus
(74) *Attorney, Agent, or Firm* — Hodgson Russ LLP

(57) ABSTRACT

The invention relates to an apparatus (1) for tracking a movable target (3), in particular tissue (5), the apparatus (1) comprising at least one applicator (7) for marking the target (3) with at least one type of markers (11), and at least one tracking system (9) which is adapted for monitoring at least the at least one type of markers (11). In order to provide an apparatus and a method for tracking a movable target (3), in particular tissue (5) which improve the reliability of the target tracking and which reduce the risk of damaging a target, it is intended according to the invention that the at least one applicator (7) is adapted for generating a randomly distributed pattern (13) of markers (11) on the target (3).

15 Claims, 2 Drawing Sheets

Figure 1:
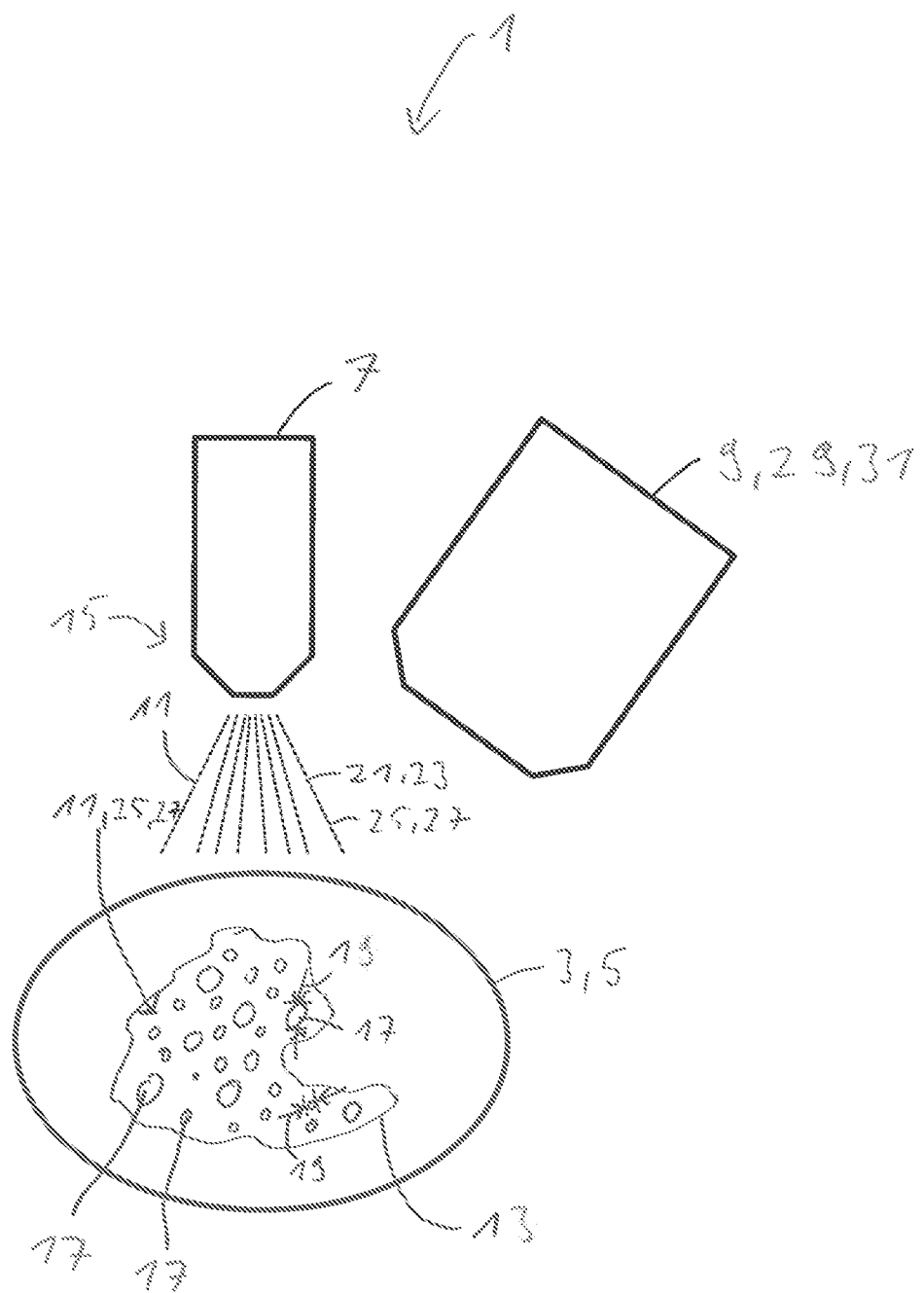

(51) Int. Cl.
*A61B 6/00* (2006.01)
*A61B 8/08* (2006.01)

(56) References Cited

U.S. PATENT DOCUMENTS

| | | |
|---|---|---|
| 2004/0138555 A1* | 7/2004 | Krag ................. A61B 90/98 600/424 |
| 2007/0093798 A1 | 4/2007 | DeBenedictis et al. |
| 2009/0171196 A1 | 7/2009 | Olson et al. |
| 2010/0234726 A1* | 9/2010 | Sirimanne ............ A61K 49/006 600/426 |
| 2010/0315524 A1 | 12/2010 | Gordon et al. |
| 2012/0002031 A1* | 1/2012 | Pertsinidis ............. G02B 21/16 348/79 |
| 2013/0131505 A1 | 5/2013 | Daon et al. |
| 2013/0274596 A1 | 10/2013 | Azizian et al. |

* cited by examiner

APPARATUS AND METHOD FOR TRACKING A MOVABLE TARGET

CROSS-REFERENCE TO RELATED APPLICATIONS

This application claims priority of European patent application number 17180286.1 filed Jul. 7, 2017, the entire disclosure of which is incorporated by reference herein.

FIELD OF THE INVENTION

The invention relates to an apparatus for tracking a movable target, in particular tissue, the apparatus comprising at least one applicator for marking the target with at least one type of markers and at least one tracking system which is adapted for monitoring at least the at least one type of markers. The invention further relates to a method for tracking a movable target, in particular tissue.

BACKGROUND OF THE INVENTION

Tracking a movable target, in particular tissue can be applied for example during surgeries for tracking a certain position on the target, in particular, if this position is to be manipulated.

It is known to track a movable or moving target by marking the target with markers. In the case of tissue tracking, it is for example known to provide a tissue with a dye, for example, by applying the dye-markers with a pen or brush-like instrument. However, this way of marking a target, in particular tissue, has several drawbacks. Firstly, generating multiple markers is time-consuming. This may in particular be disadvantageous in the case of generating markers during surgery. Another drawback is that generating markers by methods as described above bears the risk of damaging the target. Further, manually applying markers on a target may, in particular due to the time-consuming manual application, lead to a limited number of markers on the target. Finally, a limited number of markers may result in an unsatisfactory tracking of the markers. In particular in the case that at least one of the markers is removed, destroyed or cannot be tracked by the tracking system due to a barrier between the marker and the tracking system. Possible barriers are, just by way of example, smoke, vapor, liquid or solid barriers.

SUMMARY OF THE INVENTION

It is therefore an object of the invention to overcome the drawbacks mentioned above and to provide an apparatus and a method as mentioned above which can be safely applied and used, and which improve the quality of the tracking process, even if at least one marker is damaged or is blocked.

This object is reached for the apparatus mentioned in the beginning, in that the at least one applicator is adapted for generating a randomly distributed pattern of markers on the target.

For the method for tracking a movable target, the object is reached by a method which comprises the steps of randomly distributing at least one type of markers on the target with at least one applicator and tracking the randomly distributed pattern of the markers using at least one tracking system.

Generating a randomly distributed pattern is advantageous since a randomly distributed pattern may be provided much faster than following a given plan of a pattern. As a consequence, a plurality of markers can easily and quickly be provided. A randomly distributed pattern generally has a unique distribution, so such pattern may easily be tracked by a tracking system and/or recognized by an image recognition system. Since the pattern consists of a plurality of markers, the pattern may still be trackable even if at least one of the markers is removed, changed, or blocked by a variable between the marker and the tracking system.

In general, in particular in the case of surgeries, providing markers on the target does not manipulate the target itself and does not influence or cause harm on the target.

In the following, further improvements of the invention are described. The additional improvements may be combined independently of each other, depending on whether a particular advantage of a particular improvement is needed in a specific application.

According to a first advantageous improvement of the apparatus according to the invention, the at least one applicator may be adapted for providing at least one type of markers by spraying the at least one type of markers on the target. Therefore, the applicator may be or may comprise a spraying device. Spraying markers on the target has several advantages. Firstly, a plurality of markers may be distributed on the target at the same time. Further, spraying markers on the target will generally lead to a random distribution of the single markers on the target. Finally, spraying may generate a pattern on the target in a contactless way. Consequently, the at least one applicator does not have to touch the target for providing the markers on the same. This is especially advantageous in the case of marking tissue because providing the markers in a contactless way does not damage the tissue. In the case that the markers are of a non-toxic type, the markers do not negatively influence the tissue. Another advantageous consequence is that the tissue is not manipulated in a way that has a permanent influence on it.

In order to make the at least one type of markers easier to track by the at least one tracking system, the at least one applicator may be adapted for generating a plurality of randomly distributed spots of the at least one type of markers. Spots, which may have, for example, an overall shape of a circular disc may easily be identifiable and therefore easily tracked by a tracking system.

In order to increase the individuality of the generated pattern, the randomly distributed spots may have a randomly distributed spot size.

The at least one type of markers may be provided in a solution together with at least one adhesive which is adapted to adhere the markers on the target. The solution may be stored in a container that is in fluid-communication with the applicator, or the solution may be stored within the applicator and applicable through a spraying device of the applicator. This may prevent undesired removal of the markers from the target. In the case that tissue is to be tracked, the adhesive may be chosen such that it is firstly non-toxic, and secondly, is biodegradable such that it can be easily degraded after a certain amount of time.

In order to achieve a practical apparatus which is easy to apply, the at least one type of markers may be a dye and the at least one tracking system may be an optical system.

In order to further increase the quality of the target tracking, the at least one applicator may be adapted for providing at least two different types of markers, such as two or more differently colored dyes. The dyes may be applied in a subsequent manner or simultaneously. Further, the apparatus may either comprise one applicator for each colored dye or may use the same applicator for different colored dyes. The at least two different patterns of markers may be tracked by at least one tracking system. Simultaneously tracking two distinguishable patterns at the same time may increase the safety and quality of the target tracking process.

The at least one optical system is preferably a fluorescence imaging microscope. Especially in this case, the at least one type of dye is preferably a fluorophore. Using fluorescence imaging microscopy and at least one fluorophorous dye as at least one marker may increase the quality of the target tracking process. For example, if a direct view on the target is affected by disturbances or liquids or smoke which may make direct visual observation difficult, tracking with a fluorescence imaging microscope may still be possible because the fluorophores will provide a strong contrast to the remaining target and may thereby still be trackable for the apparatus. It should be noted that a fluorescence imaging microscope generally contains all elements which may be needed for imaging and tracking a fluorescence image, in particular, an illumination arrangement and generally also an image processing unit.

Additionally or in the alternative to the use of fluorescence image microscopy and fluorescence markers, the at least one type of markers may be detectable by at least one of the following techniques: X-ray-imaging, magnetic resonance imaging, ultra sound imaging and positron emission tomography, or other techniques. For example, the markers may be chosen to provide a usable contrast in an X-ray image, for example by using metallic markers. The markers could be chosen such that they provide a contrast in a magnetic resonance image. The markers could be chosen that they provide a contrast in an ultrasonic image. The markers could be chosen that they emit positrons such that they can be detected by positron emission tomography. If one of these techniques is used additionally to fluorescence imaging, then the images provided by fluorescence image microscopy and the at least one other technique could also be combined, for example for a combined image on a display for a user such as a surgeon.

It should be noted that the features of the apparatus may all be used in the method according to the invention. Consequently, the improvements of the apparatus as described above may all be used to improve the method for tracking a movable target. Accordingly, the steps of the method according to the invention are preferably performed by an apparatus according to the invention.

In the following, the invention and its improvements are described in greater detail using exemplary embodiments and with reference to the drawings. As described above, the various features shown in the embodiments may be used independently of each other in specific applications.

BRIEF DESCRIPTION OF THE DRAWING VIEWS

In the following figures, elements having the same function and/or the same structure will be referenced by the same reference numerals.

Figure 2A:
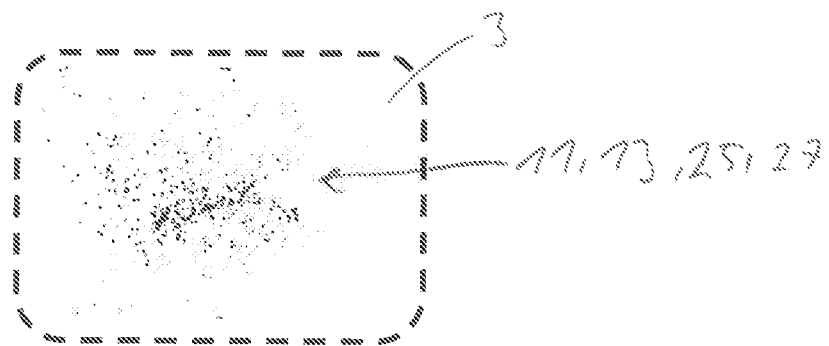
Figure 2B:
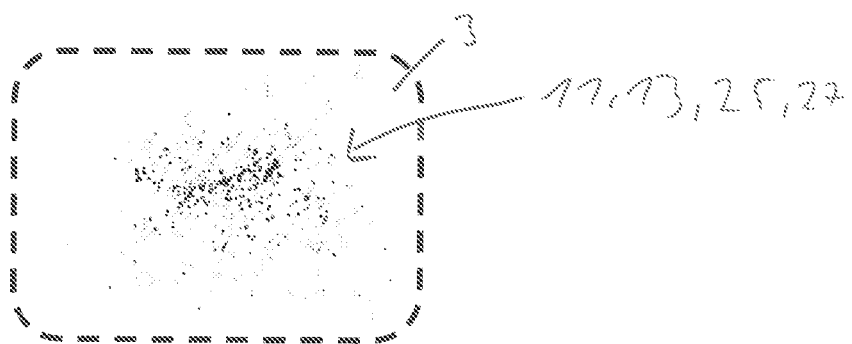
Figure 2C:
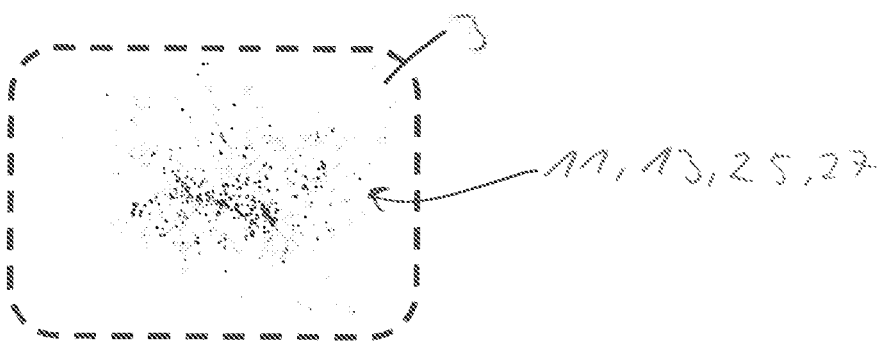

In the drawings:

FIG. 1 shows a schematic view of an exemplary embodiment of an apparatus according to the invention; and FIG. 2a-2c show exemplary patterns of randomly distributed markers according to the invention.

DETAILED DESCRIPTION OF THE INVENTION

In the following, an exemplary embodiment of an apparatus 1 according to the invention, is described with respect to FIG. 1

The apparatus 1 is intended for tracking a movable target 3, which is preferably (but not mandatory) tissue 5. The apparatus 1 comprises at least one applicator 7 and at least one tracking system 9.

The applicator 7 is adapted for marking the target 3 with at least one type of markers 11. The at least one tracking system 9 is adapted for monitoring the at least one type of markers 11. According to the invention, the at least one applicator 7 is adapted for generating a randomly distributed pattern 13 of markers 11 on the target 3.

Preferably, the at least one type of markers 11 is sprayed by the applicator 7 on the target 3 in order to provide a randomly distributed pattern 13. Therefore, the at least one applicator 7 may be or may comprise a spraying device 15.

The pattern 13 may be formed by a plurality of randomly distributed spots 17 of markers 11. The spots 17 may vary in their spot sizes, wherein the spot size is generally defined by the diameter 19 of the spots 17. Randomly distributed spot diameters 19 can guarantee that each pattern 13, which is generated by the applicator 7 is unique.

Preferably, the at least one type of markers 11 is provided in a solution 21 such that spraying the markers 11 with the applicator 7 is facilitated. The solution 21 may further comprise at least one adhesive 23 which is capable of sticking the at least one type of markers 11 on the target 3. The at least one type of markers 11 is preferably a dye 25. More preferably, the at least one type of markers 11 is a fluorophore 27.

Especially in the case that the at least one type of markers 11 is a fluorophore 27, the at least one tracking system 9 is preferably an optical system 29, more preferably a fluorescence imaging microscope 31. The fluorescence imaging microscope 31 may comprise all necessary parts for performing fluorescence imaging microscopy, such as an illumination arrangement (not shown), image recognition systems and/or others. The apparatus 1 may also be provided with detectors that use techniques that are different from fluorescence imaging. Just by way of example, the apparatus 1 may be provided with at least one system (not shown) for X-ray-imaging, magnetic resonance imaging, ultra sound imaging and/or positron emission tomography, or others. In this case, the at least one type of markers 11 is preferably chosen such that it can be detected by at least one of these additional systems. More preferable, the at least one type of markers 11 is chosen that it can be detected by at least one of these additional systems and by the fluorescence imaging microscope 31. For this purpose, the at least one type of markers 11 can either contain at least one substance that fulfils this requirement or can contain different substances, wherein each substance is chosen in order to be detectable by at least on method that is used. The at least one detector for an additional method may be a separate system or may be included in the tracking system 9.

The at least one applicator 7 is preferably adapted for providing at least two different types of markers 11, in particular two differently-colored dyes 25. The differently-colored dyes 25 may be provided simultaneously. This can, for example, be done by either providing two dyes 25 in the same solution 21 or providing the applicator 7 with two separated spraying devices 15.

Alternatively, at least two different dyes 25 may be provided subsequently. Each type of dye 25 may form its own pattern 13. Each pattern 13 may then be tracked by the tracking system 9, in particular by a fluorescence imaging microscope 31.

An example of three different patterns 13 which are provided on the same target 3 is shown in FIGS. 2a-2c.

The same target 3 is marked with three different dyes 25, wherein each dye 25 has a different color. Due to the random distribution of the spots 17, three different patterns 13 are formed wherein each pattern 13 is composed of a dye 25 of a certain color. A fluorescence imaging microscope 31 may be used to monitor each pattern 13 independently of the other patterns. Further, a fluorescence imaging microscope 31 may be used to show all three patterns 13 on a display (not shown), wherein each pattern 13 is shown in another color. This may help with improving the tracking of the target 3.

REFERENCE NUMERALS 1 apparatus
3 target
5 tissue
7 applicator
9 tracking system
11 markers
13 pattern
15 spraying device
17 spot
19 spot diameter
21 solution
23 adhesive
25 dye
27 fluorophore
29 optical system
31 fluorescence imaging microscope

What is claimed is:

1. An apparatus (1) for tracking a movable target (3) of patient tissue during surgery, the apparatus (1) comprising:
at least one applicator (7) for marking the movable target (3) during surgery with at least one type of markers (11), and
at least one tracking system (9) which is adapted for monitoring the at least one type of markers (11),
wherein the at least one applicator (7) is adapted for generating a randomly distributed pattern (13) of markers (11) on the movable target (3) and for marking the movable target (3) by spraying the at least one type of markers (11) on the movable target (3) during surgery,
wherein the randomly distributed pattern (13) of markers (11) comprises a plurality of randomly distributed spots (17) of a dye (25) on the movable target.

2. The apparatus (1) according to claim 1, wherein the randomly distributed spots (17) have randomly distributed spot sizes.

3. The apparatus (1) according to claim 2, wherein the randomly distributed spots (17) are circular in shape and have randomly distributed spot diameters (19).

4. The apparatus (1) according to claim 1, wherein the at least one type of markers (11) is provided in a solution (21) together with at least one adhesive (23) which is adapted to adhere the at least one type of markers (11) on the movable target (3).

5. The apparatus (1) according to claim 1, wherein the at least one tracking system (9) includes an optical system (29).

6. The apparatus (1) according to claim 5, wherein the at least one applicator (7) is adapted for providing at least two differently colored dyes (25) in the randomly distributed pattern (13) of markers (11) on the movable target (3).

7. The apparatus (1) according to claim 5, wherein the at least one applicator (7) is adapted for providing at least two differently colored dyes (25), each of the at least two differently colored dyes (25) being applied in a respective randomly distributed pattern (13) of markers (11) on the movable target (3).

8. The apparatus (1) according to claim 5, wherein the dye (25) includes a fluorophore (27).

9. The apparatus (1) according to claim 8, wherein the optical system (29) is a fluorescence imaging microscope (31).

10. The apparatus (1) according to claim 1, wherein the at least one type of markers (11) is detectable by at least one of the following techniques: X-ray-imaging, magnetic resonance imaging, ultra sound imaging and positron emission tomography.

11. The apparatus (1) according to claim 1, wherein the movable target (3) is tissue (5).

12. A method for tracking a movable target (3) of patient tissue during surgery, the method comprising the steps of:
randomly distributing a pattern (13) of at least one type of markers (11) on the movable target (3) using at least one applicator (7), wherein the markers (11) are distributed on the movable target (3) by spraying in a contactless manner during surgery whereby the at least one applicator (7) does not touch the movable target (3), and wherein the pattern comprises a plurality of randomly distributed spots (17) of a dye (25); and
tracking the randomly distributed pattern (13) of markers (11) using at least one tracking system (9).

13. The method according to claim 12, wherein at least two different types of markers (11) are distributed on the movable target (3).

14. The method according to claim 12, wherein the pattern (13) of markers (11) is tracked by at least one fluorescence imaging microscope (31).

15. The method according to claim 12, wherein the pattern (13) of markers (11) is tracked using at least one of the following techniques: X-ray-imaging, magnetic resonance imaging, ultra sound imaging, and positron emission tomography.

* * * * *